(12) United States Patent
Shen

(10) Patent No.: US 6,303,845 B1
(45) Date of Patent: Oct. 16, 2001

(54) HS-40 ENHANCER-CONTAINING VECTOR

(75) Inventor: Che-Kun James Shen, Taipei (TW)

(73) Assignee: Academia Sinica (TW)

( * ) Notice: Subject to any disclaimer, the term of this patent is extended or adjusted under 35 U.S.C. 154(b) by 0 days.

(21) Appl. No.: 09/536,094

(22) Filed: Mar. 24, 2000

Related U.S. Application Data

(62) Division of application No. 09/205,015, filed on Dec. 4, 1998, now abandoned.

(51) Int. Cl.$^7$ .................. A01K 67/027; A01K 67/00; C12N 5/00; C12N 15/00; C07H 21/02; C07H 21/04
(52) U.S. Cl. ............... 800/18; 800/8; 435/320.1; 435/325; 536/23.1; 536/24.5
(58) Field of Search ................ 800/8, 18; 536/23.1; 536/24.1; 435/320.1, 325

(56) References Cited

PUBLICATIONS

Wall RJ Theriogenology 45:57–68, 1996.*
Kappel et al. Current Opinion in Biotechnology 3:548–553, 1992.*
Viville, in Transgenic Animals, Houdebine (eds), Harwood academic publishers, France. pp307–321, 1997.*
Anderson WF, Nature 392:25–30, 1998.*
Verma et al Nature 389:239–242, 1997.*
Kay et al, PNAS 94:12744–12746, 1997.*
Pondel et al. Nucleic Acid Res. 24(2):4158–64, 1996.*
Zang et al. Mol. Cell. Bio. 13(4):2298–2308, 1993.*
Jarman et al Mol. Cell. Bio. 11(9):4679–4689, 1991.*
Andrews et al., "Erythoid Transcriptional Factor . . . ," Nature, 362:722–728, 1993.
Chan et al., "Cloning Nrfl . . . ," Proc. Natl. Acad. USA, 90:11371–11375, 1993.
Chen et al., "Reactivion of Silenced . . . ," Proc. Natl. Acad. Sci. USA, 94:5798–5803, 1997.
Ellis et al., "A Dominant Chromatin–opening . . . ," The EMBO Journal, 15:562–568, 1996.
Gourdon et al., "Analysis of a 70 kb. . . ," Nucleic Acids Research, 22:4139–4147, 1994.
Huang et al., "Modulation of an Enhancer–promoter . . . ," The 11$^{th}$ Conference on Hemoglobin Switching Rosario, Orcas Island, Washington, Oct. 2–6, 1998.
Jarman et al., "Characterization of the . . . , " Molecular and Cellular Biology, 11:4679–4689, 1991.
Ney et al., "Tandem AP–1–binding . . . ," Genes & Development, 4:993–1006, 1990.
Palmer et al., "Genetically Modified Skin . . . ," Proc. Natl. Acad. Sci. USA, 88:1330–1334, 1991.
Pondel et al., "The Developmental Regulation . . . ,"Nucleic Acids Research, 20:5655–5660, 1992.
Robertson et al., "Position–dependent . . . ," Proc. Natl. Acad. Sci. USA, 92:5371–5375, 1995.
Sabl et al., "Copy Number and . . . ," Genetics; 142:447–458,. 1996.
Sharpe et al., "Analysis of the Human . . . ," Proc. Natl. Acad. Sci. USA, 90:11262–11266, 1993.
Sharpe et al., "Analysis of the Human . . . ," The EMBO Journal, 11:4565–4572, 1992.
Wen et al., "Modulation of an Enhancer–Promoter . . . ," 18$^{th}$ International Congress of Genetics, Beijing, China, Aug. 10–15, 1998.
Zhang et al., "Functional Roles of in . . . ," The Journal of Biological Chemistry, 270:8501–8505, 1995.
Zhang et al., "Transcriptional Activation . . . ,"Modlecular and Cellular Biology, 13:2298–2308, 1993.
Zhang et al., "Transcriptional Regulation . . . ," Mole Biol of Hemoglobin Switching, Intercept, Ltd., Andover, MA, pp. 193–202, 1995.
Anderson, WF, Nature, 392:25–30, 1998.
Verma et al., Nature, 389:239–242, 1997.
Kay et al., PNAS, 94:12744–12746, 1997.
Zang et al., Mol. Cell. Bio., 13(4):2298–2308, 1993.
Jarman et al., Mol. Cell. Bio., 11(9):4679–4689, 1991.
Miller et al., Biotechniques, 7(9):980–990, 1989.

* cited by examiner

*Primary Examiner*—Deborah J. R. Clark
*Assistant Examiner*—Sumesh Kaushal
(74) *Attorney, Agent, or Firm*—Fish & Richardson P.C.

(57) ABSTRACT

The invention relates to a transgenic animal whose somatic and germ line genomic DNA includes at least one copy of a transgene having (1) a transcriptional start site; (2) a promoter operably linked to the transcriptional start site; and (3) an enhancer operably linked to the promoter, the enhancer including the nucleotide sequence of SEQ ID NO:1, where the transgenic animal expresses a transcript driven by the promoter, the level of expression in at least one cell type of the animal being positively correlated with the copy number of the transgene.

14 Claims, No Drawings

HS-40 ENHANCER-CONTAINING VECTOR

This application is a divisional of U.S. Ser. No. 09/205,015, filed Dec. 4, 1998, now abandoned.

BACKGROUND OF THE INVENTION

HS-40 is a 350–400 bp enhancer element located about 40 kb upstream of ζ-globin gene, which is expressed in the human embryonic erythroblasts but not in the human adult erythroblasts. Specific elements within the HS-40 enhancer have been identified, including GATA-1 motifs, NF-E2/AP1 motifs (a 3' and a 5' motif), and a Sp1 binding site.

SUMMARY OF THE INVENTION

The invention is based on the discovery that a single nucleotide change in the 3'NF-E2/AP1 element of the human HS-40 enhancer, unlike the wild type HS-40 enhancer, confers position-independent and copy number-dependent expression on a transgene. In addition, the single nucleotide change allows expression of the gene in the cells of an adult mouse, an effect not seen for the wild type HS-40 enhancer.

Accordingly, the invention features a viral expression vector (e.g., a retrovirus) having a nucleic acid including (1) a transcriptional start site; (2) a promoter (e.g., a tissue-specific promoter such as a ζ-globin promoter) operably linked to the transcriptional start site; and (3) an enhancer operably linked to the promoter, the enhancer including the mutated NF-E2/AP1 (mtNF-E2/AP1) DNA sequence TCT-GAGTCA (SEQ ID NO:1) or the RNA equivalent thereof The underlined "T" represents a mutation of the wild type "G" in the wild type NF-E2/AP1 (wtNF-E2/AP1) sequence. In a specific embodiment, the enhancer includes the minimal mutated HS-40 DNA sequence AGATAACTGGGCCAACCATGACTCAGT-
  GCTTCTGGAGGCCAACAGGACTTCT GAGT-
  CATCCTGTGGGGGTGGAGGTGGGA-
  CAAGGGAAAGGGGTGAATGGTAC
  TGCTGATTACAACCTCTGGTGCTGCCTC-
  CCCCTCCTGTTTATCT (SEQ ID NO:2)

or an RNA equivalent thereof. The bold sequence represents the mtNF-E2/AP1 site with the G to T mutation underlined. The minimal HS-40 enhancer sequence excludes a 5' GATA1(b) site because it has been shown that this site is not necessary for HS-40 enhancer activity (Zhang et al., J Biol Chem 270:8501–8505, 1995).

The enhancer can also include the fall mutated HS-40 enhancer sequence:

TCGACCCTCTGGAACCTATCAGGGACCA-
  CAGTCAGCCAGGCAAGCACATCTG CCCAAGC-
  CAAGGGTGGAGGCATGCAGCT-
  GTGGGGGTCTGTGAAAACACTTGA
  GGGAGCAGATAACTGGGCCAACCAT-
  GACTCAGTGCTTCTGGAGGCCAACAGG ACT-
  TCTGAGTCATCCTGTGGGOGTG-
  GAOGTGGGACAAGGGAAAGGGGTGAA
  TGGTACTGCTGATTACAACCTCTGGT-
  GCTGCCTCCCCCTCCTGTTTATCTGAG AGG-
  GAAGGCCATGCCCAAAGTGTTCACAGC-
  CAGGCTTCAGGGGCAAAGCCT
  GACCCAGACAGTAAATACGTTCT-
  TCATCTGGAGCTGAAGAAATTC (SEQ ID NO:3)

or an RNA equivalent thereof The bold sequence represents the mtnf-E2/AP1 site with the G to T mutation underlined. This sequence is referred to herein as the mtHS-40 sequence, which differs from the wild type HS-40 (wtHS-40) sequence by the G/T mutation indicated above. Again, the single mutation is underlined. The vector can also contain a transcriptional termination signal (e.g., a polyadenylation signal). In other embodiments, the promoter drives transcription of a MRNA encoding a polypeptide (e.g., a growth hormone), the transcription beginning from the transcriptional start site.

A promoter is a nucleotide sequence required to facilitate transcription from a transcriptional start site, which is the site at which the first nucleotide of the transcript is transcribed, the nucleotide being complementary to the corresponding nucleotide in the nucleic acid. A promoter operably linked to a transcriptional start site means that the promoter is capable of driving transcription from the transcriptional start site in the absence of farther nucleotide sequences.

An enhancer is a nucleic acid sequence which increases the level of transcription from a promoter. Enhancers need not be in any specified position in the nucleic acid in relation to the promoter, transcriptional start site, or transcriptional termination site. All that is required for a specific enhancer to be operably linked to a specific promoter is that the presence of the enhancer increases transcription driven by that promoter.

A transcriptional termination signal is a nucleic acid sequence which terminates transcription of a transcript. A variety of promoters, enhancers, and transcriptional termination signals are known in the art.

A viral expression vector is any combination of a nucleic acid and at least one protein which is useful for delivering a nucleic acid into a cell so as to express a transcript encoded by the nucleic acid in the cell. Other components, such as a lipid bilayer can also be present in the vector. An example of a viral expression vector is a retrovirus.

The invention also includes a transgenic animal (e.g., a mouse or other rodent, pig, rat, cow, chicken, turkey, or sheep) whose somatic and germ line cells contain at least one copy of a transgene comprising (1) a transcriptional start site; (2) a promoter (e.g., a tissue-specific promoter such as a ζ-globin promoter) operably linked to the open reading frame; and (3) an enhancer operably linked to the promoter. The enhancer includes the nucleotide sequence of SEQ ID NO:1 (e.g., SEQ ID NO:2). The transgenic animal expresses a transcript driven by the promoter, where the level of expression in at least one cell type (e.g., a erythroblast) of the animal is proportionally dependent on the copy number of the transgene, i.e., the greater the copy number, the greater the expression. Such a transcript can be a mRNA encoding a polypeptide (e.g., a growth hormone). In other embodiments, the somatic and germ line cells contain more than 5 copies (e.g., more than 15 copies) of the transgene.

The invention also features a method of expressing a transcript in an animal (e.g., a mouse, pig, rat, cow, chicken, turkey, or sheep) by administering to the animal a nucleic acid comprising (1) an transcriptional start site for the transcript; (2) a promoter (e.g., a tissue-specific promoter such as a ζ-globin promoter) operably linked to the transcriptional start site; and (3) an enhancer operably linked to the promoter, the enhancer comprising the DNA sequence of SEQ ID NO:1 or 2 or the RNA equivalent thereof. The transcript can be a mRNA encoding a polypeptide. The nucleic acid can be administered by parenteral injection (e.g., intramuscular injection) or via a viral expression vector. The nucleic acid can further include a transcriptional termination signal (e.g., a polyadenylation signal).

Nucleic acids and viral vectors containing an enhancer having the mtNF-E2/AP1 sequence described above can be used to express a therapeutic antisense RNA or mRNA encoding a therapeutic polypeptide in an animal in a position-independent and transgene copy number dependent manner. This was an unexpected result because, previously, transgene expression was limited by position-effect variegation, silencing of transgenes, and the inability to increase expression by increasing the copy number of the transgene. See, e.g., Sabl et al., Genetics 142:447–458, 1996; Palmer et al., Sharpe et al., EMBO J 11:4565–4572, 1992; and Chen et al., Proc Natl Acad Sci USA 94:5798–5803, 1997. By inclusion of an enhancer containing the mtNF-E2/AP1 sequence in the transgene sequence, these deficiencies in transgene expression are removed. Enhancement of transgene expression can result in transgenic animal models exhibiting more severe symptoms so that therapeutic efficacy in those models can be measured in a wider range of symptom severity. Examples of such models, which can be improved by the present invention, are described in U.S. Pat. Nos. 5,811,634 and 5,675,060

Other features or advantages of the present invention will be apparent from the following detailed description and also from the claims.

DETAILED DESCRIPTION

The invention relates to nucleic acids and viral vectors containing an enhancer with a mutated NF-E2/AP1 site (e.g., the mtHS40 enhancer), and their use in expressing RNA in an animal. Nucleic acids including the mtNF-E2/AP1 site can be used to form transgenic animals of the invention which express an antisense transcript or a mRNA encoding the protein to be expressed in the transgenic animal. The expression of the transgene is not affected by its position in the genome, nor is the expression inhibited at high transgene copy numbers (e.g., above 5, 7, 9, 14, or 19 copies). Instead, the expression level is directly correlated with transgene copy number, thereby allowing high levels of expression at high transgene copy numbers.

Introduction of a transgene into the fertilized egg of an animal (e.g., a mammal) is accomplished by any number of standard techniques in transgenic technology. See, e.g., Hogan et al., Manipulating the Mouse Embryo: A Laboratory Manual, Cold Spring Harbor Laboratory Press, Cold Spring Harbor, N.Y., 1986. Most commonly, the transgene is introduced into the embryo by way of microinjection.

Once the transgene is introduced into the egg, the egg is incubated for a short period of time and is then transferred into a pseudopregnant animal of the same species from which the egg was obtained (Hogan et al., supra). In the case of mammals, typically 125 eggs are injected per experiment, approximately two-thirds of which will survive the procedure. Twenty viable eggs are transferred into pseudopregnant mammal, four to ten of which will develop into live pups. Typically, 10–30% of the pups (in the case of mice) carry the transgene.

To identify the transgenic animals of the invention, progeny are examined for the presence of the transgene using standard procedures such as Southern blot hybridization or PCR. Expression of the transgene can also be assessed using Northern blots, Western blots, and immunological assays.

Without further elaboration, it is believed that one skilled in the art can, based on the above disclosure and the description below, utilize the present invention to its fullest extent. The following example is to be construed as merely illustrative of how one skilled in the art can practice the invention and are not limitative of the remainder of the disclosure in any way. Any publications cited in this disclosure are hereby incorporated by reference.

Production of Transgenic Mice

Transgenic mice were produced by microinjection of DNA fragments into the pronuclei of fertilized mouse eggs as described in Brinster et al., Cell 27:223–231, 1981 and Costantini et al., Nature 294:92–94, 1981. Plasmids pHS40-ζ597-GH and pHS40(r-mt 1)-ζ597-GH are described in Zhang et al., Mol Cell Biol 13:2298–2308, 1993. Digestion of these plasmids with EcoRI, NdeI, and ScaI yielded 3.12 kb DNA fragments containing the HS-40 enhancer, the ζ-globin promoter, and the growth hormone (GH) open reading frame. The 3.12 kb DNA fragments were eluted from soft agarose gels, purified, and used for microinjection.

Transgenic founders were identified and their transgene copy number determined by Southern blot analysis of tail DNA. The founders were then bred with nontransgenic C57/B6 mice to establish lines. The morning on which the copulatory pluf was observed was designated 0.5 day postcoital. For analysis of fetal (14.5 days postcoital) and embryonic (9.5 days postcoital) mice, transgenic males were mated to nontransgenic C57/B6 females. Transgenic pups were identified by PCR analysis of fetal mice tails or of embryo DNA. For each identification, duplicate PCR reactions were carried out using one 5' primer from the ζ-globin promoter region, and two different 3' primers from the GH region (see below).

A total of 9 founders with wild type HS40-ζGH (wt) and 10 founders with the mutant HS40-ζGH (mt) have been obtained. The copy numbers of integrated fragments in wtHS-40-containing mice vary from 1 to more than 100, as shown in Table 1.

TABLE 1

| Mutant HS-40 Transgene | | | Wild Type HS-40 Transgene | | |
| --- | --- | --- | --- | --- | --- |
| Founder line | Copy number | hGH, ng/ml | Founder line | Copy number | hGH, ng/ml |
| 1A* | 1 | 470 | 1A* | 1 | 36 |
| 1B* | 1 | 530 | 1B* | 1 | 20 |
| 1C* | 1 | 1,060 | 2 | 2 | 14 |
| 2 | 2 | 650 | 3 | 3 | 22 |
| 3 | 3 | 1,260 | 5 | 5 | 5 |
| 8* | 8 | 2,990 | 10* | 10 | 13 |
| 10* | 10 | 3,360 | 13* | 13 | 187 |
| 13* | 13 | 4,650 | 100A | >100 | 1,400 |
| 15* | 15 | 5,560 | 100B | >100 | 30 |
| 19* | 19 | 6,490 | | | |

In Table 1, the founders for which lines have been established are indicated by an asterisk. Mice with the wtHS-40 transgene were assayed at the age of 5 months except founder 1B, which was evaluated at 9 months old. Mice with the mtHS-40 transgene were assayed at the age of 4 months except founder 15, which was evaluated at 2 months old.

The ζ-globin promoter activities in the founder mice were first measured with a blood GH assay as described in Zhang et al., supra. The levels of human GH in the blood were quantitated with the Allegro hGH radioimmunoassay kit from Nichols Institute. When the concentration of GH in the blood exceeded 50 ng/ml, the samples were first diluted with horse serum in order perform the assay in a linear range.

It was known that the amount of secreted enzyme molecules are good representations of the quantities of mRNAs inside the expressing cells (Zhang et al., supra; Palmiter et al., Nature 300:611–615, 1982; Palmiter et al., Science 222:809–814, 1983; Hammer et al., Nature 315:680–683, 1985; and Selden et al., Mol Cell Biol 6:3137–3179, 1986). The level of GH in wtHS-40 transgenic mice were all low and comparable to non-transgenic controls. This was consistent with observations that the human ζ-globin promoter activity is essentially shut off in adult transgenic mice, even when it is linked in cis with the wtHS-40 enhancer or with the β-globin locus control region (Pondel et al., Nucl Acids Res 20:5655–5660, 1992; Robertson et al., Proc Natl Acad Sci USA 92:5371–5375, 1995; Albitar et al., Mol Cell Biol 11:3786–3794, 1991; and Spanger et al., Nucl Acids Res 18:7093–7097, 1990).

In contrast, the blood GH levels of the ten founder mice having the mtHS-40 enhancer exhibited a roughly linear, positive relationship relative to transgene copy number. Further, the expression of the mtHS-40 transgene was integration site-independent (i.e., position-independent) because the integration sites here were believed to be random and mice having similar transgene copy numbers exhibit similar level of expression. The blood GH levels in these founders at other ages, as well as these founders' progeny, were similar to the levels of expression in mtHS-40-containing mice, as shown in Table 1.

To analyze the GH RNA levels in transgenic fetuses and embryos, liquid N2-frozen embryos, fetuses, or fetal livers were manually homogenized, and the RNA isolated by standard acid guandinium isothiocyanate-phenol-chloroform extraction (Sambrook et al., Molecular Cloning: A Laboratory Manual, Cold Spring Harbor Laboratory Press, Plainview, N.Y., 2nd ed., 1989). For adult samples, the mice were rendered anemic by three injections of phenylhydrazine (40 μg/g of body weight) so that erythroblasts would enter the adult blood and be collected for analysis. The second injection was 8 hours after the first injection, and the third injection was 24 hours after the first. Six days after the first injection, the mice were sacrificed, and the RNA was isolated from different tissues. In all cases, the total RNA was used for the following assay without further purification.

RT-PCR was carried out as described in Chelly et al., Nature 333:858–860, 1988 and Foley et al., Trends Genet 9:380–385, 1993. Each reverse transcription reaction mixture contained 1 μg of RNA, 200 units of SUPERSCRIPT II® reverse transcriptase (Gibco BRL), and 20 mM oligo d(T)$_{15}$. One-twentieth of the cDNA was then amplified by PCR using Taq polymerase (Gibco BRL) and primers specific for human GH, mouse $β^{major}$, mouse ζ-globin promoter, or mouse G3PDH. Amplifications were carried out in a HYBRID OmniGene system with the following temperature profiles: an initial denaturation at 95° C. for 3 min, 53° C. for 1 min, and 72° C. for 1 min; followed by repeating cycles of 95° C. for 1 min, 53° C. for 1 min, and 72° C. for 1 min; and finally an elongation step at 72° C. for 5 min. Each PCR analysis was done in duplicate. The sequences of PCR primers used are as follows. For mG3PDH, TGAAGGTCGGTGTGAACGGATTTGOC (SEQ ID NO:4) was used as the 5' primer, and CATGTAGGCCATGAGGTCCACCAC (SEQ ID NO:5) was used at the 3' primer. For the human GH gene, GTCCCTGCTCCTGGCTTT (SEQ ID NO:6) was used as the 5' primer, and ATGCGGAGCAGCTCCAGGTT (SEQ ID NO:7) was used as the 3' primer. Another 3' primer used for the human GH gene was CATCAGCGTTTGGATGCCTT (SEQ ID NO:8). For the mouse $β^{major}$ sequence, TGGGCAGGCTGCTGGTTA (SEQ ID NO:9) was used at the 5' primer, and TTAGTGGTACTTGTGAGCCAA (SEQ ID NO:10) was used as the 3' primer. For the mouse ζ-globin promoter sequence, CTGATGAAGAATGAGAGAGC (SEQ ID NO:11) was used as the 5' primer, and TAGAGGTACTTCTCATCAGTCAG (SEQ ID NO:12) was used as the 3' primer.

The PCR product lengths were 980 bp for mouse G3PDH, 335 bp for mouse $β^{major}$, and 290 bp or 450 bp for ζ-GH. One-fifth of each PCR reaction was resolved on a 1.5% agarose-ethidium bromide gel, which was then documented using a IS1000 Digital Imaging System and saved as a TIF computer file. The band intensities were quantitated by the PhosphorImage System.

For semi-quantitative purposes, mouse G3PDH was used as the internal standard. The linearity of amplification of the G3PDH cDNA was first defined by amplification of serial dilutions of the cDNA samples. Twenty five cycles were chosen for amplifying mouse G3PDH since, under the reaction conditions described above, the signals were linear over a wide range of dilutions of cDNA. In the initial calibration test, G3PDH bands with similar intensities were obtained from the different tissue cDNA when the same amount of RNA was used for reverse transcription. The appropriate PCR cycle number used to amplify the human GH, mouse $β^{major}$, and mouse ζ-globin transcripts were 28, 25 and 28, respectively. The amount of different cDNA used for amplification were first determined by PCR using the mouse G3PDG primers, then individual PCR reactions were performed using the human GH, mouse $β^{major}$r, or mouse ζ-globin primers.

It was known that, in the developing mouse, the first site of erythropoiesis is at the yolk sac blood island at 8–14 days of gestation. The major site of erythropoiesis then shifts to the fetal liver, and finally to the spleen at birth. The expression of GH transcripts from the mouse ζ-globin promoter in adult transgenic mice containing the mtHS-40 enhancer was examined. In all adult mice having the mtHS-40 transgene, the expression of GH RNA was restricted to the eiythroid tissues. Expression was roughly limited to the spleen and blood, with no expression in the liver or brain. Expression could not be detected in the blood of mice containing the mtHS-40 transgene unless the mice were first rendered anemic, indicating that expression was erytliroblasts-specific. Mice having the wtHS-40 transgene exhibited little, if any, expression.

The expression of the transgenic mice at the fetal stage also appeared to be erythroid-specific. ζ-GH transcripts could be detected in 14.5 day fetuses from transgenic mice with either mtHS-40 or wtHS-40 sequences. No ζ-GH transcripts were detected in non-transgenic control mice. A high intensity RT-PCR band was apparent in the reaction containing fetal liver RNA, consistent with the erythroid fetal liver being the major site of transcription of ζ-GH transgenes.

Changes in ζ-GH transgene expression were followed by RT-PCR. Transgenic mice having the wtHS-40 transgene exhibited the expected temporal pattern of expression during development, the level of ζ-GH transcripts was relatively high at the 9.5 day embryo stage but dropped significantly in the adult blood. In contrast, the transgenic mice having the mtHS-40 enhancer continued to express the ζ-GH transcript into adulthood. In addition, even with only one copy of the transgene, mice having the mtHS-40 expressed at a higher level than mice having the wtHS-40 enhancer, regardless of the stage of development.

These data indicated that the mtHS-40 enhancer sequence not only relieved the repression of the ζ-globin promoter in adulthood, but enhanced expression at all stages of development, even at one transgene copy per genome. When combined with the linear relationship between transgene copy number and expression level, as described above, the results indicated that mtHS-40 can be used as an enhancer of gene expression in a variety of contexts.

OTHER EMBODIMENTS

It is to be understood that while the invention has been described in conjunction with he detailed description thereof, the foregoing description is intended to illustrate and not limit the scope of the invention, which is defined by the scope of the appended claims. Other aspects, advantages, and modifications are also within the scope of this invention. For example, inconsequential deletions, additions, or substitutions of nucleotides within SEQ ID NOs: 1, 2, or 3 (i.e., do not affect the advantageous properties of the mtHS-40 enhancer) are within the scope of the claims.

What is claimed is:

1. A transgenic mouse whose somatic and germ line genomic DNA comptises at least one copy of a transgene comprising (1) a nucleic acid sequence encoding a polypeptide; (2) a ζ-globin promoter operably linked to the nucleic acid sequence; and (3) an enhancer operably linked to the promoter, the enhancer comprising the nucleotide sequence of SEQ ID NO:1, wherein the transgenic mouse expresses the polypeptide, the level of expression in the erythroid cells of the mouse being correlated with the copy number of the transgene.

2. The transgertic mouse of claim 1, wherein the DNA contains more than 5 copies of the transgene.

3. The transgenic mouse of claim 2, wherein the DNA contains more than 15 copies of the transgene.

4. The transgenic mouse of claim 1, wherein the erythroid cells include a erythroblast.

5. The transgenic mouse of claim 1, wherein the enhancer comprises SEQ ID NO:2.

6. The transgenic mouse of claim 5, wherein the enhancer comprises SEQ ID NO:3.

7. The transgenic mouse of claim 1, wherein the expression of the transgene is independent of its position in the genomic DNA.

8. The transgenic mouse of claim 1, wherein the transgene is expressed in a cell of an adult form of the transgenic mouse.

9. An isolated cell whose genonic DNA comprises at least one copy of a transgene comprising (1) a nucleic acid suence encoding a polypeptide; (2) a ζ-globin promoter operably linked to the nucleic acid sequence; and (3) an enhancer operably linked to the promoter, the enhancer comprising the nucleotide sequence of SEQ ID NO:1, wherein the cell expresses the polypeptide, the level of expression being correlated with the copy number of the transgene.

10. The cell of claim 9, wherein the DNA contains more than 5 copies of the transgene.

11. The cell of claim 10, wherein the DNA contains more than 15 copies of the transgene.

12. The cell of claim 9, wherein the enhancer comprises SEQ ID NO:2.

13. The cell of claim 12, wherein the enhancer comprises SEQ ID NO:3.

14. The cell of claim 9, wherein the expression of the transgene is independent of its position in the genomnic DNA.

* * * * *

SEQUENCE LISTING

<160> NUMBER OF SEQ ID NOS: 12

<210> SEQ ID NO 1
<211> LENGTH: 9
<212> TYPE: DNA
<213> ORGANISM: Homo sapiens

<400> SEQUENCE: 1 tctgagtca                                                                                    9

<210> SEQ ID NO 2
<211> LENGTH: 147
<212> TYPE: DNA
<213> ORGANISM: Homo sapiens

<400> SEQUENCE: 2
agataactgg gccaaccatg actcagtgct tctggaggcc aacaggactt ctgagtcatc      60
ctgtgggggt ggaggtggga caagggaaag gggtgaatgg tactgctgat tacaacctct     120
ggtgctgcct cccctcctg tttatct                                          147

<210> SEQ ID NO 3
<211> LENGTH: 356
<212> TYPE: DNA
<213> ORGANISM: Homo sapiens

<400> SEQUENCE: 3
tcgaccctct ggaacctatc agggaccaca gtcagccagg caagcacatc tgcccaagcc      60
aagggtggag gcatgcagct gtggggtct gtgaaaacac ttgagggagc agataactgg     120
gccaaccatg actcagtgct tctggaggcc aacaggactt ctgagtcatc ctgtgggggt     180
ggaggtggga caagggaaag gggtgaatgg tactgctgat tacaacctct ggtgctgcct     240 cccctcctg tttatctgag agggaaggcc atgcccaaag tgttcacagc caggcttcag     300
gggcaaagcc tgacccagac agtaaatacg ttcttcatct ggagctgaag aaattc         356

<210> SEQ ID NO 4
<211> LENGTH: 26
<212> TYPE: DNA
<213> ORGANISM: Mus musculus

<400> SEQUENCE: 4
tgaaggtcgg tgtgaacgga tttggc                                           26

<210> SEQ ID NO 5
<211> LENGTH: 24
<212> TYPE: DNA
<213> ORGANISM: Mus musculus

<400> SEQUENCE: 5
catgtaggcc atgaggtcca ccac                                             24

<210> SEQ ID NO 6
<211> LENGTH: 18

-continued

```
<212> TYPE: DNA
<213> ORGANISM: Homo sapiens

<400> SEQUENCE: 6
gtccctgctc ctggcttt                                                    18

<210> SEQ ID NO 7
<211> LENGTH: 20
<212> TYPE: DNA
<213> ORGANISM: Homo sapiens

<400> SEQUENCE: 7
atgcggagca gctccaggtt                                                  20

<210> SEQ ID NO 8
<211> LENGTH: 20
<212> TYPE: DNA
<213> ORGANISM: Homo sapiens

<400> SEQUENCE: 8
catcagcgtt tggatgcctt                                                  20

<210> SEQ ID NO 9
<211> LENGTH: 18
<212> TYPE: DNA
<213> ORGANISM: Mus musculus

<400> SEQUENCE: 9
tgggcaggct gctggtta                                                    18

<210> SEQ ID NO 10
<211> LENGTH: 21
<212> TYPE: DNA
<213> ORGANISM: Mus musculus

<400> SEQUENCE: 10
ttagtggtac ttgtgagcca a                                                21

<210> SEQ ID NO 11
<211> LENGTH: 20
<212> TYPE: DNA
<213> ORGANISM: Mus musculus

<400> SEQUENCE: 11
ctgatgaaga atgagagagc                                                  20

<210> SEQ ID NO 12
<211> LENGTH: 23
<212> TYPE: DNA
<213> ORGANISM: Mus musculus

<400> SEQUENCE: 12
tagaggtact tctcatcagt cag                                              23
```